United States Patent [19]
Amenomori

[11] Patent Number: 5,211,167
[45] Date of Patent: May 18, 1993

[54] ULTRASONIC DIAGNOSING APPARATUS

[75] Inventor: Takeshi Amenomori, Hachioji, Japan

[73] Assignee: Olympus Optical Co., Ltd., Tokyo, Japan

[21] Appl. No.: 838,920

[22] Filed: Feb. 21, 1992

[30] Foreign Application Priority Data

Feb. 28, 1991 [JP] Japan ................................. 3-55575
Feb. 3, 1992 [JP] Japan ................................. 4-17643

[51] Int. Cl.$^5$ ............................................. A61D 8/00
[52] U.S. Cl. ............................ 128/660.04; 128/662.06
[58] Field of Search ................... 128/660.04–660.5, 128/661.07–661.10, 662.05, 662.06

[56] References Cited

U.S. PATENT DOCUMENTS

| | | | |
|---|---|---|---|
| 4,062,237 | 12/1977 | Fox ........................... | 128/660.05 X |
| 4,501,277 | 2/1985 | Hongo ........................ | 128/661.09 X |
| 4,671,292 | 6/1987 | Matzuk ....................... | 128/662.05 X |
| 4,991,604 | 2/1991 | Wurster et al. .............. | 128/660.03 |

FOREIGN PATENT DOCUMENTS 59-222140 12/1984 Japan .
60-72541 4/1985 Japan .
63-317140 12/1988 Japan .

Primary Examiner—Francis Jaworski
Attorney, Agent, or Firm—Stevens, Davis, Miller & Mosher

[57] ABSTRACT

An ultrasonic diagnosing apparatus for displaying an ultrasonic image of an organ of a patient including an ultrasonic probe for transmitting an ultrasonic wave toward a cavity wall of the patient and receiving an ultrasonic wave reflected by the cavity wall to produce an echo signal. A plurality of organ marks denoting a plurality of organs and a plurality of posture marks representing postures of the patient on a bed are previously stored in a memory. Any desired organ mark and posture mark are selectively read out of the memory and the thus selected organ mark and posture mark are displayed on a display screen of a monitor together with the ultrasonic image as a composite image. In superimposition on the organ mark there is further displayed an ultrasonic wave transmitting point indicating mark. By monitoring the composite image displayed on the monitor screen, it is possible to know a part of the organ whose ultrasonic image is displayed as well as a point and a direction from and in which the ultrasonic wave is transmitted. Therefore, the diagnosis can be performed very easily and accurately.

7 Claims, 7 Drawing Sheets

FIG._4
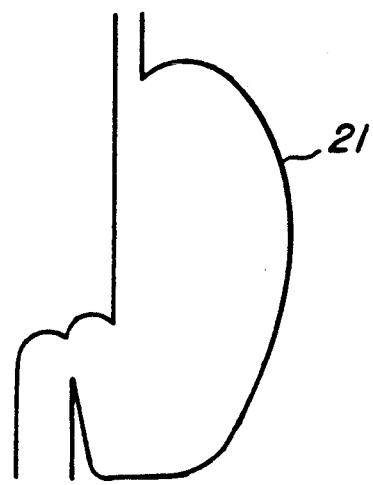
FIG._5
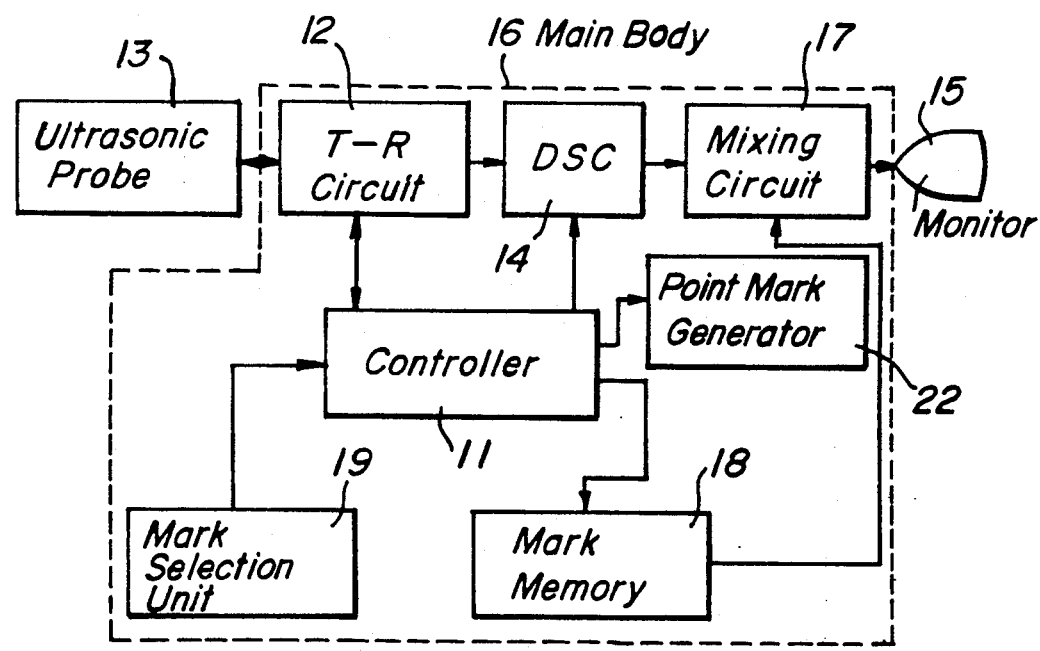

ULTRASONIC DIAGNOSING APPARATUS

BACKGROUND OF THE INVENTION

Field of the Invention

The present invention relates to an ultrasonic diagnosing apparatus for displaying an ultrasonic image of a cavity within a patient by transmitting an ultrasonic wave toward a cavity wall and receiving an ultrasonic wave reflected by the cavity wall.

Description of the Related Art Statements

Heretofore, an ultrasonic diagnosing apparatus has been widely used for diagnosing diseases of various organs of human beings. In this case there are many modes of usage. In a typical mode, the ultrasonic diagnosis is carried out in a testing room while one or more doctors are watching a patient as well as ultrasonic images of the patient. There are many cases in which an operator takes photographs of ultrasonic images of a patient in the testing room and the photographs thus taken are checked or analyzed by a doctor in a room separated from the testing room. Further, due to the development of the communication system, a video signal representing the ultrasonic images of the patient and picked-up in the testing room is transmitted to the diagnosing room to display the ultrasonic images on a television monitor provided in the diagnosing room and the doctor performs the diagnosis by monitoring the ultrasonic images. There is a case that the video signal is recorded on a video tape by a video tape recorder, and after that ultrasonic images are reproduced on the monitor and the doctor can perform the diagnosis by watching the thus reproduced ultrasonic images.

In the typical usage of the ultrasonic diagnosing apparatus, the doctor watches the patient, and thus the doctor can positively know what organ of the patient is monitored from what direction, because the posture of the patient on a bed can be easily known by seeing the patient. However, when the doctor is not existent in the testing room, the doctor could not know accurately what organ of the patient is under inspection and the patient lies on the bed in what posture, so that it is sometimes difficult to determine the condition of the patient in a correct manner.

In order to avoid the above mentioned inconvenience, in Japanese Patent Application Laid-open Publication Kokai Sho 59-222140 published on Dec. 13, 1984, there is proposed to display together with an ultrasonic image a body mark denoting an organ under test and a probe mark indicating a position of an ultrasonic probe on the patient body. As shown in FIG. 1, these body mark 1 and probe mark 2 are selected from a plurality of previously prepared figures which represent various combinations of the body marks and probe marks.

In Japanese Patent Application laid-open Publication Kokai Sho 60-72541 published on Apr. 24, 1985, there is disclosed another known ultrasonic diagnosing apparatus in which a typical image of organ is displayed in the three-dimensional manner, a point at which the ultrasonic probe is positioned on the patient body is displayed by a line mark and a direction in which the ultrasonic wave is transmitted is denoted by a plurality of parallel arrows starting from the line.

In Japanese Patent Application Laid-open Publication Kokai Sho 63-317140 issued on Dec. 26, 1988 a body mark is displayed on the monitor on which the ultrasonic image is displayed and a point under inspection is indicated by a special mark on the body mark.

However, the above mentioned known ultrasonic diagnosing apparatuses in which the body mark, probe mark, organ pattern, line mark and arrows are useful to some extent for a case in which the ultrasonic probe is brought into contact with the outer surface of patient body, but are very inconvenient for a case in which the ultrasonic probe is inserted into the cavity of patient, because in the latter case it is rather difficult to know accurately to what portion of an organ under test is inspected from what direction. Particularly, in the known ultrasonic diagnosing apparatuses, the posture of the patient on the bed is not indicated, so that the direction into which the ultrasonic wave is transmitted could not be understood easily.

SUMMARY OF THE INVENTION

The present invention has for its object to provide a novel and useful ultrasonic diagnosing apparatus having an ultrasonic probe which is insertable into a cavity of a patient, in which it is possible to know easily and accurately a portion of an organ of the patient under inspection, and thus a very accurate diagnosis can be performed in an easy manner with the aid of ultrasonic images displayed on a monitor.

According to the invention, an ultrasonic diagnosing apparatus comprises:

an ultrasonic prove which is insertable into a cavity of a patient for transmitting an ultrasonic wave toward a cavity wall and receiving an ultrasonic wave reflected by the cavity wall to generate an echo signal;

an image signal processing circuit connected to said ultrasonic probe for receiving said echo signal and processing the echo signal to produce an ultrasonic image signal;

a memory means for storing a plurality of posture marks which represent postures of the patient on a bed and a plurality of organ marks which represent organs of the patient;

a selecting means for selecting a desired posture mark among said plurality of posture marks and a desired organ mark among said plurality of organ marks to produce a posture mark signal and an organ mark signal;

an image processing means for mixing said posture mark signal representing said desired posture mark and said organ mark signal representing said desired organ mark with the ultrasonic image signal generated by said image signal processing means to produce a composite image signal; and a displaying means for receiving said composite image signal to display a composite image of ultrasonic image, posture image and organ image.

In the ultrasonic diagnosing apparatus according to the invention, the desired posture and organ marks are selected from a plurality of posture and organ marks and the thus selected marks are displayed on a monitor screen together with the ultrasonic image. Therefore, a doctor can easily and accurately know an organ within which the ultrasonic wave is transmitted and the posture of the patient lying on the bed, and thus the diagnosis can be carried out accurately by monitoring the composite image displayed on the monitor screen.

BRIEF DESCRIPTION OF THE DRAWINGS

FIG. 4 is a schematic view representing an organ mark according to the invention;

FIG. 5 is a block diagram showing the construction of a second embodiment of the ultrasonic diagnosing apparatus according to the invention;

DESCRIPTION OF THE PREFERRED EMBODIMENTS

Figure 1:
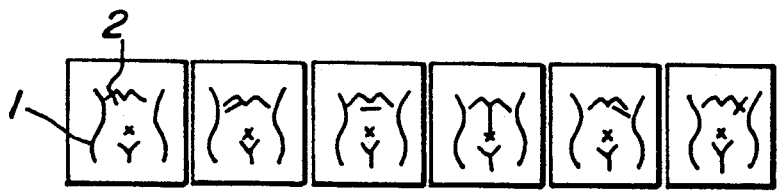
FIG. 1 is a schematic view showing body marks and probe marks displayed in a known ultrasonic diagnosing apparatus.
Figure 2:
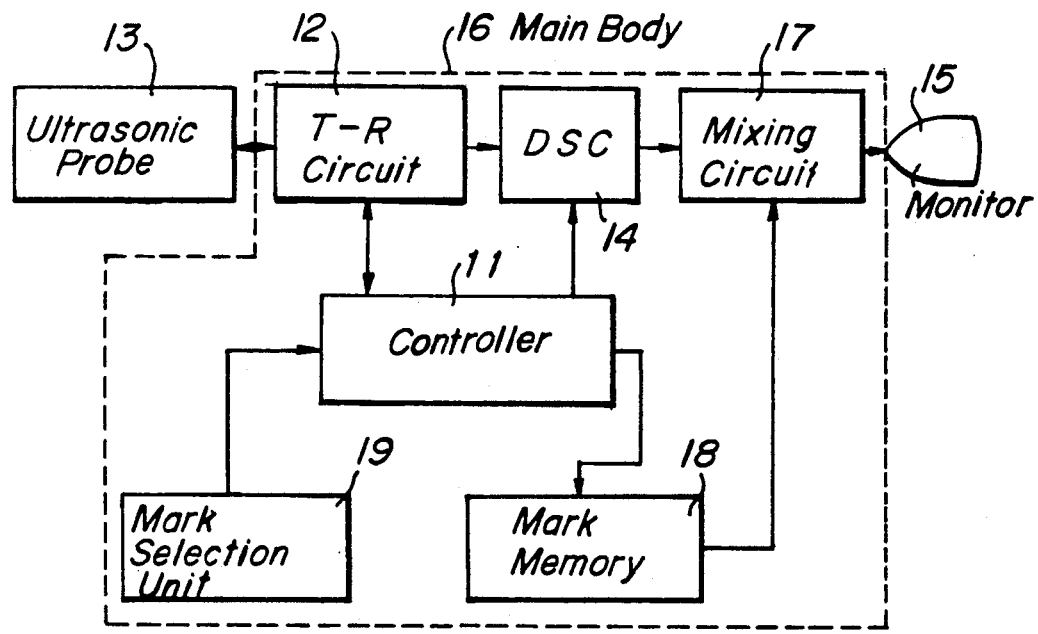
FIG. 2 is a block diagram illustrating the construction of a first embodiment of the ultrasonic diagnosing apparatus according to the invention.

FIG. 2 is a block diagram showing the construction of a first embodiment of the ultrasonic diagnosing apparatus according to the present invention. In the present embodiment, under the control of a controller 11, a transmitting pulse is generated by a transmitting-receiving circuit 12 and is supplied to an ultrasonic vibrator (not shown) provided in a distal end of an ultrasonic probe 13 which is contracted to be insertable into a cavity of a patient under inspection. Then, a pulsatory ultrasonic wave is transmitted from the ultrasonic probe 13 toward a cavity wall, and an ultrasonic wave reflected by the cavity wall is received by the ultrasonic vibrator in the probe 13 and is converted into an echo signal. The echo signal is supplied to the transmitting-receiving circuit 12 and is processed thereby in a usual manner. Then the echo signal is further supplied to a digital scan converter (DSC) 14 to which position information is also supplied from the controller 11. In DSC 14 the echo signal is processed and is converted into an ultrasonic image signal. The thus generated ultrasonic image signal is stored in DSC 14, and is then supplied to a monitor 15 to display thereon an ultrasonic image of the cavity of the patient. It should be noted that the ultrasonic probe 13 may be detachably coupled with a main body 16 of the ultrasonic diagnosing apparatus.

Figures 3A, 3B, 3C:
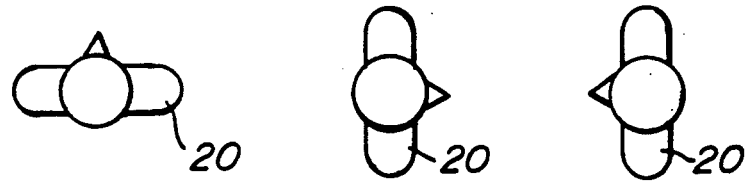
FIGS. 3A, 3B and 3C are schematic views depicting posture marks according to the invention.

In the present embodiment, between the digital scan converter 14 and the monitor 15 there is arranged an image mixing circuit 17. Further, a display mark memory 18 and a mark selection unit 19 are connected to the controller 11. The mark selection unit 19 may be formed by a keyboard. In the memory 18 there are previously stored a plurality of posture marks 20 as shown in FIGS. 3A, 3B and 3C which represent various postures of a patient on a bed, and a plurality of organ marks. In FIG. 4 there is shown an example of the organ mark 21 which represents a stomach.

In the present embodiment, an operator or doctor manually selects one of the posture marks 20 as well as one of the organ marks 21 by operating the mark selection unit 19. Then, the corresponding posture mark and organ mark are read out of the memory 18 under the control of the controller 11. Then, image signals representing the thus read out marks are supplied to the mixing circuit 17 and are mixed with the ultrasonic image signal to produce a composite image signal of the ultrasonic image signal and the mark signals. Then, the composite image signal is supplied to the monitor 15 and a composite image of the ultrasonic image and the posture and organ marks 20 and 21 is displayed on a display screen of the monitor.

In the present embodiment, the operator or doctor knows the posture of the patient on the bed and the organ of the patient under inspection and selects manually corresponding posture mark 20 and organ mark 21 by operating the mark selection unit 19. Then, the thus selected posture mark 20 and organ mark 21 are displayed on the monitor 15 together with the ultrasonic image. Therefore, it can be easily known that what portion of the patient is monitored from what direction by the ultrasonic probe 13, so that the diagnosis can be performed easily and accurately by monitoring the composite image displayed on the monitor screen. In this case, the composite image signal may be transmitted from the testing room in which the patient and operator are existing to the diagnosing room in which one or more doctors are existing and the composite image may be displayed on a monitor provided in the diagnosing room. Alternatively, the composite image signal may be recorded on a video tape and the composite signal may be reproduced later on in any desired room. Further the composite image may be recorded on a photographic film and after developing the film, the diagnosis may be carried out by watching the composite image on the photographic film.

FIG. 5 is a block diagram illustrating a second embodiment of the ultrasonic diagnosing apparatus according to the invention. Portions of the present embodiment similar to those of the previous embodiment shown in FIG. 2 are denoted by the same reference numerals used in FIG. 2. In the present embodiment, there is additionally provided an ultrasonic wave transmitting point indicating mark generating unit 22 for generating a signal which represents an ultrasonic wave transmitting point mark. This unit 22 is connected to the controller 11 and to the image mixing circuit 17. By operating the mark selection unit 19, the unit 22 generates an ultrasonic wave generating point indication signal under the control of the controller 11 and the thus generated signal is supplied to the image signal mixing circuit 17 and is mixed with the composite image signal of ultrasonic image signal and mark signals.

Figures 6A, 6B:
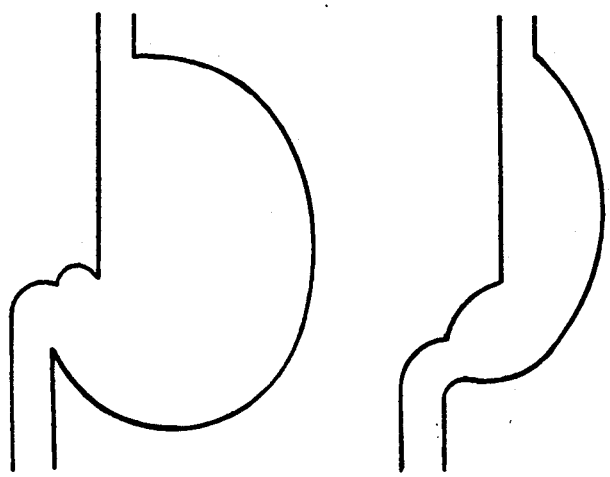
FIGS. 6A and 6B are schematic views depicting organ marks according to the invention.

The shape and size of organs are different from each other depending on the sex, male or female and the races. For instance, the white race has a stomach typically shown by a stomach mark shown in FIG. 6A and the stomach of the yellow race may be typically represented by a stomach mark illustrated in FIG. 6B. In the other words, the shape and size of the stomach of the white race differ from those of the yellow race. Therefore, in the present embodiment, a plurality of organ marks belonging to the same organ are previously stored in the mark memory 18 and any desired one of the organ marks is selected by the mark selection unit 19. The remaining construction of the present embodiment is similar to that of the previous embodiment.

Figure 7:
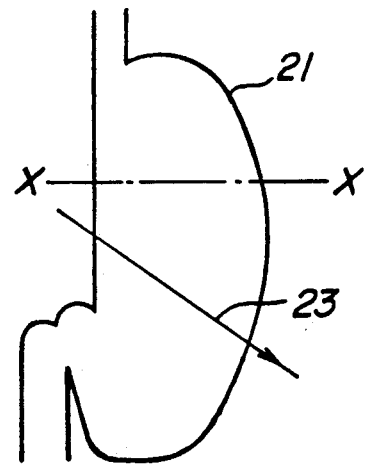
FIG. 7 is a schematic view illustrating an organ mark on which an ultrasonic wave transmitting point indicating mark is indicated in a superimposition manner.
Figure 8:
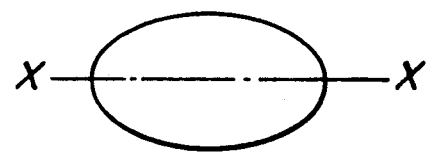
FIG. 8 is a schematic view for explaining the function of the organ mark shown in FIG. 7.

In the present embodiment, as shown in FIG. 7, an organ mark 21 is selectively displayed on the monitor 15 together with the ultrasonic image and at the same time a mark 23 for indicating the point and direction from and in which the ultrasonic wave is transmitted is displayed in a superimposed manner on the organ mark 21. In this case, when the patient is lying on the bed with the face upward as illustrated by the posture mark 20 shown in FIG. 3A, the ultrasonic wave propagating medium such as water is existing on a part of the stomach which is near the back of the patient. That is to say, when a cross sectional of the stomach cut along a line X-Y in FIG. 7 is considered as shown in FIG. 8, it is known that the water is existent in an upper portion of the stomach. In this connection it should be noted that in the cross section of FIG. 8 an upper portion is near the rear side of the patient and lower portion is near the front side of the patient. Therefore, one can easily understand that the ultrasonic image is taken at a part of the stomach which is near the back of the patient. When the patient is lying on the bed with the right side upward as illustrated in FIG. 3B, the water is existent in a part of the stomach which is near the left side, and similarly when the patient is lying on the bed with the left side upward as shown in FIG. 3C, the water is existent in a part of the stomach which is near the right side. In this manner, the part of the stomach whose ultrasonic image is taken can be easily and accurately known by monitoring the composite image displayed on the monitor 15.

Figure 9:
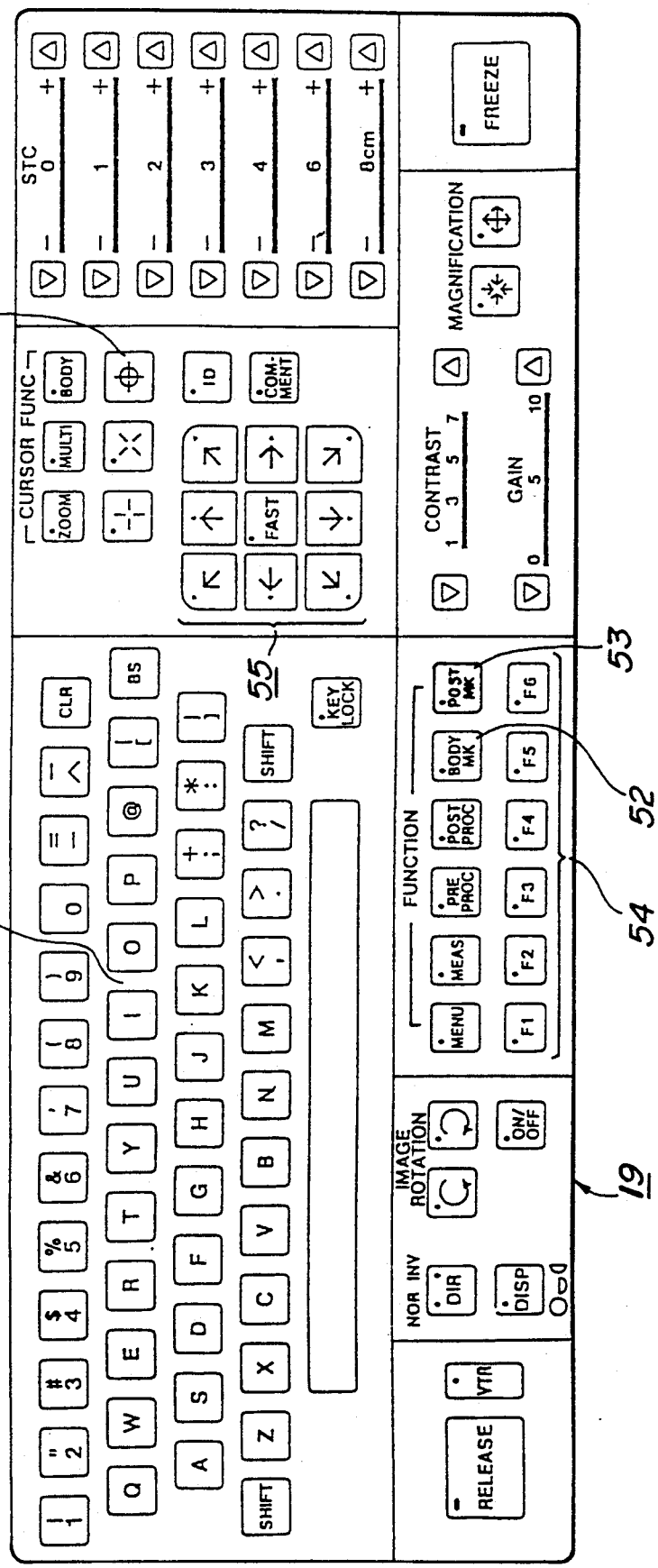
FIG. 9 is a plan view illustrating an embodiment of the selection unit shown in FIG. 5.

FIG. 9 is plan view depicting an embodiment of the mark selection unit 19. The mark selection unit 19 comprises a group of input keys 51 for entering various kinds of patient data such as the sex and race of the patient, a switch 52 for generating a group of organ marks, a switch 53 for generating a group of posture marks, mark selection switches 54 for selecting organ and posture marks, switches 55 for moving and rotating the ultrasonic wave transmitting point indicating mark 23, and a switch 56 for changing the function of the switches 55 between the linear movement and the rotation.

Figure 10:
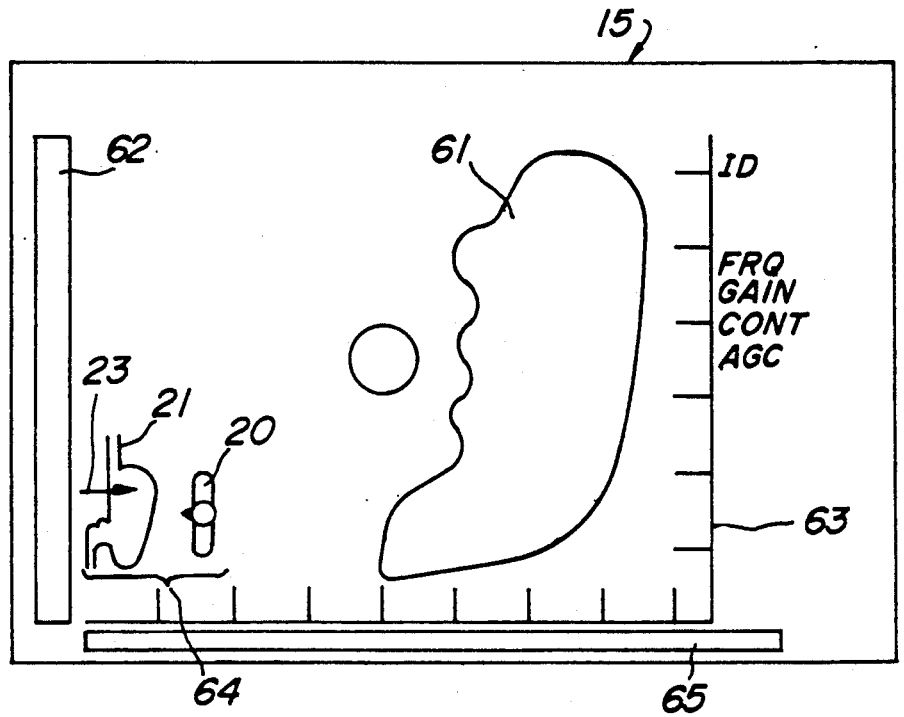
FIG. 10 is a schematic view showing an example of a composite image displayed on the monitor screen.

FIG. 10 is a schematic view showing an example of the composite image displayed on the display screen of the monitor 15. On the screen of the monitor 15 there are displayed ultrasonic image 61, gray scale bar 62, and range scale 63. On the monitor screen there are further provide a mark display region 64 for displaying selected posture mark 20 and organ mark 21, and a mark group display region 65 for displaying a group of marks. On the organ mark 21 there is displayed the ultrasonic wave transmitting point indicating mark 23 in superimposition thereon.

Figure 11:
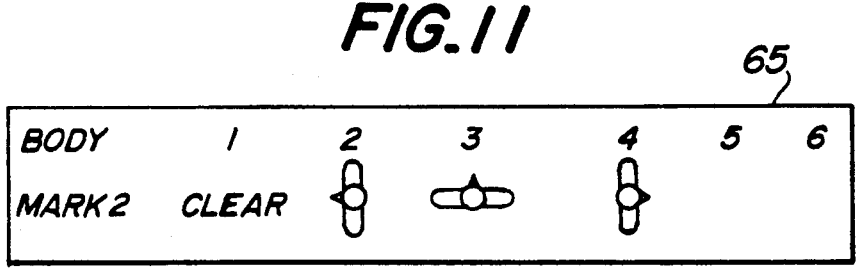
FIG. 11 is a schematic view depicting an example of the posture mark group.

At first, the switch 53 on the mark selection unit 19 is operated to display a group of posture marks on the mark group display region 65 as depicted in FIG. 11.

Figure 12:
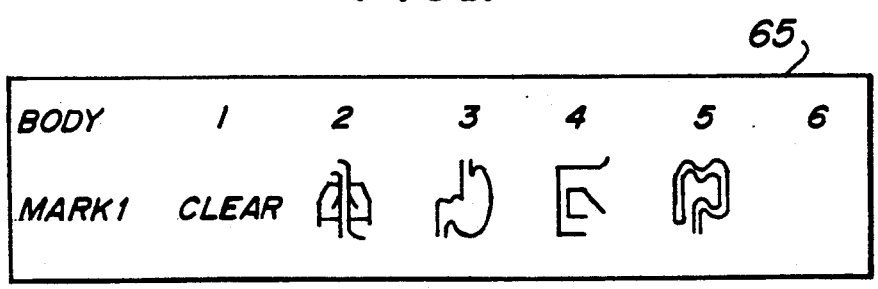
FIG. 12 is a schematic view representing an example of the organ mark group.

Then, a desired posture mark is selected by operating any one of the mark selection switches 54, and a selected posture mark 20 is read out of the mark memory 18 and is displayed in the mark display region 64 of the display screen of the monitor. When the switch 52 is operated, the group of organ marks 21 is displayed on the mark group display region 65 as illustrated in FIG. 12. In this case, organ marks corresponding to the previously entered sex and race data of the patient are selectively read out of the mark memory 18. Then, a desired one of the mark selection switches 54 is operated to select a desired organ mark and the thus selected organ mark 21 is read out of the mark memory 18 and is displayed on the mark display region 64 in the display screen. Next the ultrasonic wave transmitting point indicating mark 23 is displayed on the organ mark 21 displayed in the mark display region 64 by suitably operating the linear movement-rotation changing switch 56 as well as the movement-rotation switches 55. That is to say, at first an indication mark in the form of a bar is displayed on the screen. Then, the switch 56 is operated to set the switches 55 into the linear-movement mode and the indication mark is parallelly shifted by operating the switches 55. After the indication mark is shifted into a desired position, the switch 56 is operated to change the mode of the switches 55 into the rotation mode, and the indication mark is rotated by operating the switches 55.

In this manner, the composite image including the ultrasonic image 61, posture mark 20, organ mark 21 and ultrasonic wave transmitting point indicating mark 23 as shown in FIG. 10 can be displayed on the display screen of the monitor 15. Therefore, one can understand what part of what organ of the patient is taken as the ultrasonic image, so that a very accurate diagnosis can be performed by monitoring the composite image.

Figure 13:
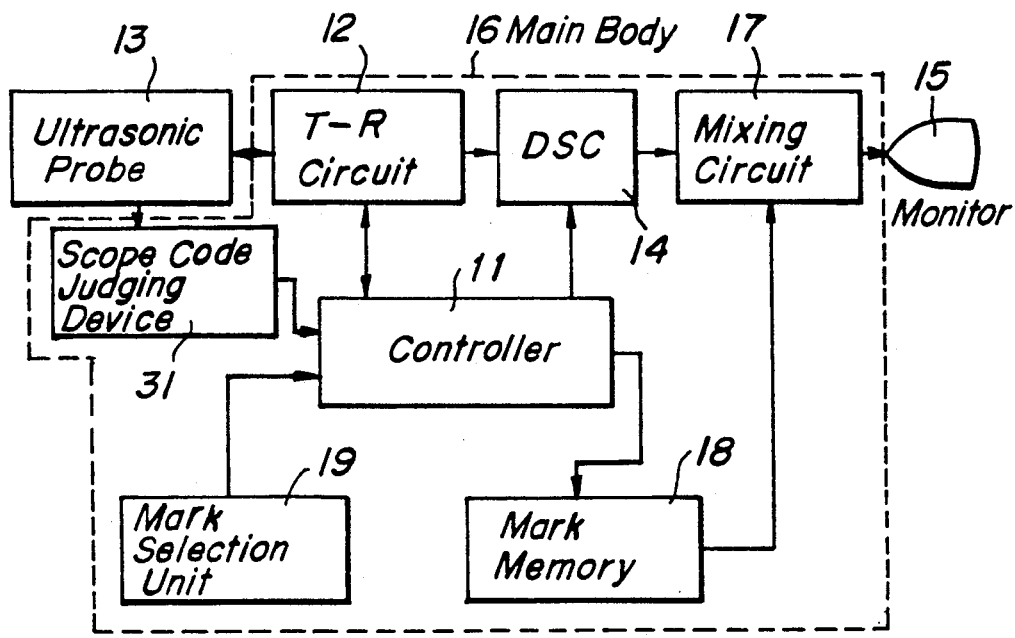
FIG. 13 is a block diagram illustrating the construction of a third embodiment of the ultrasonic diagnosing apparatus according to the invention.

FIG. 13 is a block diagram showing a third embodiment of the ultrasonic diagnosing apparatus according to the invention. Also in the present embodiment, portions similar to those shown in FIG. 2 are denoted by the same reference numerals used in FIG. 2. In the present embodiment, the organ mark 21 is automatically selected instead of the manual selection. To this end, there is provided a scope code judging device 31 for automatically judging a kind of the ultrasonic probe 13, and in the ultrasonic probe 13 there is provided a scope code generating device. When the ultrasonic prove 13 is coupled with the main body 16, the scope code judging device 31 detects a scope code generated by the scope code generating device provided in the ultrasonic probe 13. The thus detected scope code is supplied to the controller 11. Then, the controller 11 operates to automatically select a desire organ mark from the group of organ marks stored in the memory 18. The remaining construction of the present embodiment is same as that of the first embodiment illustrated in FIG. 2.

In the present embodiment, the organ mark is automatically selected by coupling the ultrasonic probe 13 to the main body 16, so that the operation of the operator becomes simple. Further a possible error in the manual selection of the organ mark can be effectively prevented.

Figure 14:
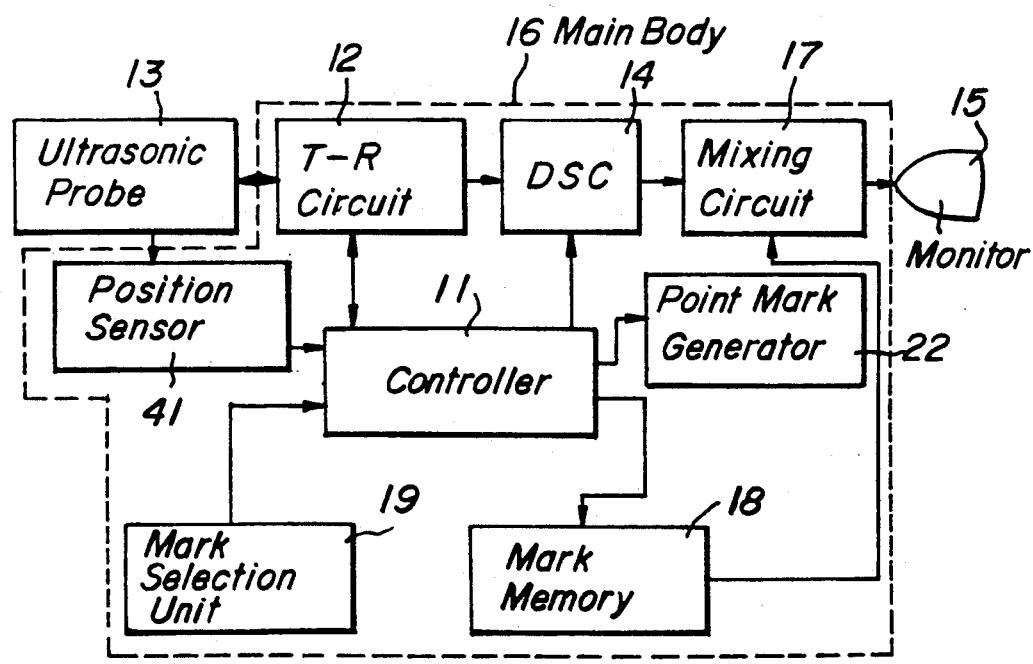
FIG. 14 is a block diagram showing the construction of a fourth embodiment of the apparatus according to the invention.

FIG. 14 is a block diagram showing a fourth embodiment of the ultrasonic diagnosing apparatus according to the invention. In the present embodiment, the ultrasonic wave transmitting point indicating mark 23 is automatically generated by detecting the movement of the angle knob (not shown) provided in the ultrasonic probe 13 for moving a distal end of the ultrasonic probe and a length of a portion of an insertion section of the ultrasonic probe 13 which has been inserted into the cavity of the patient. To this end, the ultrasonic probe 13 is constructed to generate up/down and right/left signals in relation to the operation of the angle knob and the length of the insertion section of the probe which has been inserted into the cavity, and in the main body 16 there is arranged a distal end position sensor 41 for detecting the movement of the angle knob of the ultrasonic probe 13 and a point within the cavity up to which the distal end of the probe has been inserted. An output signal of the distal end position sensor 41 is supplied to the controller 11, and the controller controls the ultrasonic wave transmitting point indicating mark generating device 22 to produce automatically an ultrasonic wave transmitting point indicating mark signal related to the operation of the angle knob of the ultrasonic probe and the length of the insertion section of the probe which has been inserted into the cavity. Also in the present embodiment, the manual operation of the operator can be saved and any possible error due to the manual operation can be avoided.

In the embodiment illustrated in FIG. 5, a plurality of marks of the same organ belonging to different races are previously stored in the memory 18, however according to the invention only organ marks which are specific to a single race in whose territory the ultrasonic diagnosing apparatus is to be used may be stored in the mark memory.

FIGS. 15 to 20 show some examples of the composite image displayed on the display screen of the monitor. It should be noted that in these composite images the posture mark is not included.

Figure 15:
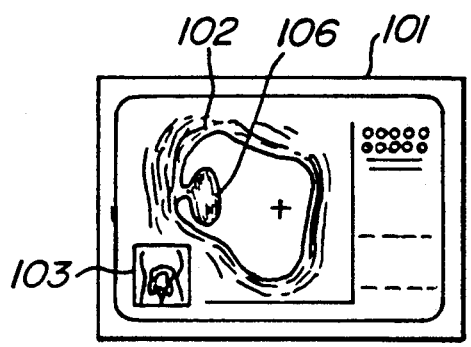
FIGS. 15 to 20 are schematic views depicting examples of the composite images displayed on the monitor screen.
Figure 16:
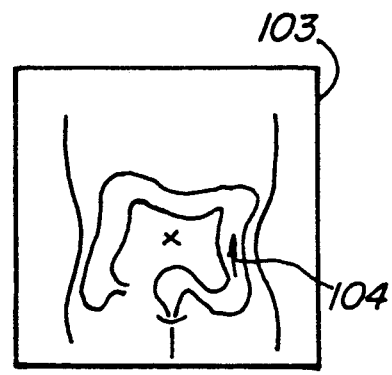

In FIG. 15, there is displayed an ultrasonic image of a colon having a polyp 106 and at the same time there is displayed a colon mark 103 at a left lower region of the monitor screen. FIG. 16 is an enlarged view of the colon mark 103 shown in FIG. 15. In super-imposition of the colon mark there is also shown an ultrasonic wave transmitting point indicating mark 104 indicating a point and a direction from and in which the ultrasonic wave is transmitted.

Figure 17:
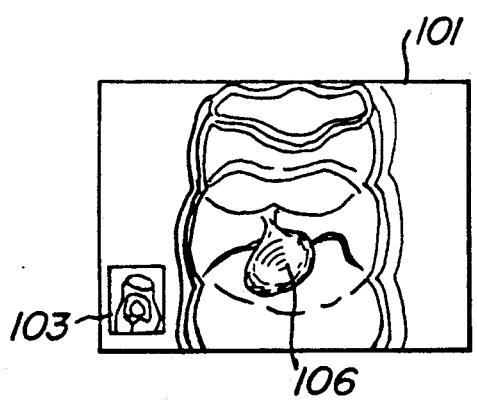
Figure 18:
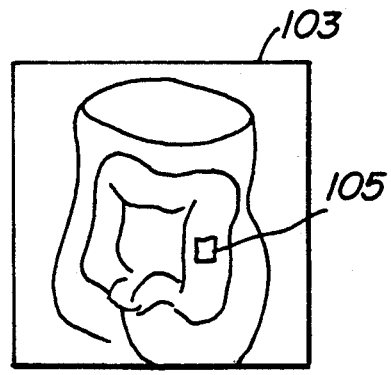

In FIG. 17, the ultrasonic image is displayed as a three-dimensional image by processing the echo signal while a distal end of the ultrasonic probe of the radial scanning type is linearly moved within a cavity. In a left lower portion of the display screen, there is also displayed an organ mark 103. FIG. 18 is an enlarged view of the organ mark 103 shown in FIG. 17. The organ mark 103 is also displayed as a simple three-dimensional image and a point of the organ under inspection is displayed by an area mark 105.

Figure 19:
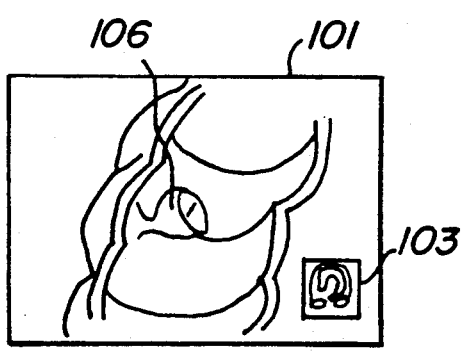
Figure 20:
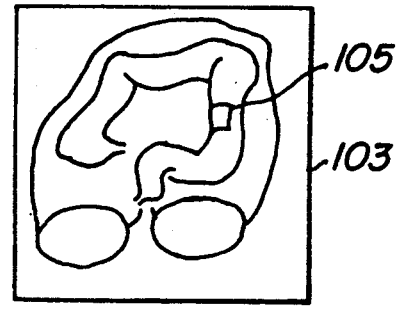

FIG. 19 is a three-dimensional ultrasonic image which is obtained by rotating the three-dimensional ultrasonic image illustrated in FIG. 17. In a right lower portion of the display screen there is displayed a three-dimensional organ mark 103. As shown in FIG. 20 the organ mark is also rotated in relation to the rotation of the ultrasonic three-dimensional ultrasonic image.

In FIG. 16 the position and direction of the ultrasonic wave transmitting point indicating mark 104 may be set by operating a suitable operating member such as a track ball. Further the rotation of the ultrasonic image shown in FIGS. 17 and 19 may be performed by operating the track ball. In this case, the organ mark 103 is also rotated accordingly, so that the position and size of the polyp can be judged in an easy and accurate manner.

Further the relative position of the polyp with respect to ambient organs and blood vessels can be understood at a glance, and thus the diagnosis can be performed precisely and a very large amount of useful data for diagnosis and surgical operation can be obtained.

As explained above in detail, in the ultrasonic diagnosing apparatus according to the present invention, the ultrasonic image is displayed together with the posture mark, organ mark and ultrasonic wave transmitting point mark, so that the doctor can recognize a point of an organ under inspection and can effect an accurate diagnosis in an easy and accurate manner.

What is claimed is:

1. An ultrasonic diagnosing apparatus comprising: an ultrasonic probe which is insertable into a cavity of a patient for transmitting an ultrasonic wave toward a cavity wall and receiving an ultrasonic wave reflected by the cavity wall to generate an echo signal;
    an image signal processing circuit connected to said ultrasonic probe for receiving said echo signal and processing the echo signal to produce an ultrasonic image signal;
    a memory means for storing a plurality of posture marks which represent postures of the patient on a bed and a plurality of organ marks which represent organs of the patient;
    a selecting means for selecting a desired posture mark among said plurality of posture marks and a desired organ mark among said plurality of organ marks to produce a posture mark signal and an organ mark signal;
    an image processing means for mixing said posture mark signal representing said desire posture mark and said organ mark signal representing said desired organ mark with the ultrasonic image signal generated by said image signal processing means to produce a composite image signal; and
    a displaying means for receiving said composite image signal to display a composite image of ultrasonic image, posture mark and organ mark.

2. An apparatus according to claim 1, wherein said mark selecting means comprises a means for displaying a plurality of organ mark signals stored in said memory means, a means for selecting one of the thus displayed organ marks, a means for displaying said plurality of posture marks, and a means for selecting one of the thus displayed posture marks.

3. An apparatus according to claim 2, wherein said memory means is constructed to store a plurality of organ marks belonging to each of a plurality of organs depending upon the sex and race.

4. An apparatus according to claim 1 further comprising a means for displaying an ultrasonic wave transmitting point indicating mark for indicating a point at which the ultrasonic wave is transmitted in superimposition with the selected and displayed organ mark.

5. An apparatus according to claim 4, wherein said means for displaying the ultrasonic wave transmitting point indicating mark comprises a means for displaying a point indication mark, means for parallelly moving the point indication mark and a means for rotating the point indication mark.

6. An apparatus according to claim 4, wherein said means for displaying the ultrasonic wave transmitting point indicating mark comprises a distal end position sensor for detecting an operation of an angle knob for moving a distal end of the ultrasonic probe as well as a length of the ultrasonic probe which is inserted into the cavity of the patient and a means for responding to an output signal of said distal end position sensor to generate an ultrasonic wave transmitting point indicating mark signal.

7. An apparatus according to claim 1, wherein said ultrasonic probe is provided to be detachably coupled with a main body of the apparatus and has an organ indicating means for denoting an organ specific to a relevant ultrasonic probe, and said organ mark selecting means comprises a means for detecting said organ denoted by said organ indicating means and a means for automatically selecting an organ mark on the basis of an output signal of said means for detecting the organ denoted by said organ indicating means.

* * * * *